US 8,027,722 B1

(12) United States Patent
Nabutovsky (10) Patent No.: US 8,027,722 B1
(45) Date of Patent: Sep. 27, 2011

(54) MULTIFOCAL PVC DETECTION FOR PREVENTION OF ARRHYTHMIAS

(75) Inventor: Yelena Nabutovsky, Sunnyvale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 2283 days.

(21) Appl. No.: 10/687,846

(22) Filed: Oct. 17, 2003

(51) Int. Cl.
*A61N 1/362* (2006.01)

(52) U.S. Cl. ............................................. 607/9; 607/14

(58) Field of Classification Search .................. 607/9, 14
See application file for complete search history.

(56) References Cited

U.S. PATENT DOCUMENTS

| | | | | |
|---|---|---|---|---|
| 4,784,153 A * | 11/1988 | Marks | ............................ | 600/514 |
| 5,271,411 A * | 12/1993 | Ripley et al. | .................. | 600/515 |
| 5,351,696 A | 10/1994 | Riff et al. | ........................ | 128/702 |
| 5,417,714 A * | 5/1995 | Levine et al. | ...................... | 607/9 |
| 5,560,369 A | 10/1996 | McClure et al. | .............. | 128/704 |
| 5,645,070 A | 7/1997 | Turcott | .......................... | 128/702 |
| 5,712,801 A | 1/1998 | Turcott | ......................... | 364/550 |
| 5,772,691 A * | 6/1998 | Routh et al. | ......................... | 607/9 |
| 5,873,895 A * | 2/1999 | Sholder et al. | .................... | 607/9 |
| 6,122,546 A * | 9/2000 | Sholder et al. | ..................... | 607/9 |
| 6,266,554 B1 | 7/2001 | Hsu et al. | ........................ | 600/515 |
| 6,370,431 B1 * | 4/2002 | Stoop et al. | ....................... | 607/14 |
| 6,438,410 B2 | 8/2002 | Hsu et al. | ........................ | 600/516 |
| 6,453,192 B1 | 9/2002 | Ding et al. | ....................... | 600/516 |
| 2002/0193696 A1 | 12/2002 | Hsu et al. | ......................... | 600/512 |
| 2004/0215273 A1 * | 10/2004 | Van Bolhuis et al. | ............ | 607/27 |

OTHER PUBLICATIONS

Katz, "Arrhythmias II: Clinical Manifestations and Principles of Therapy", Physiology of The Heart, pp. 580-629 (Lippincott Williams & Williams, 3rd ed., 2001).
Kessler, et al., "Multiform Ventricular Complexes: A Transitional Arrhythmia Form?", American Heart Journal, vol. 118, No. 3, pp. 441-444 (Sep. 1989).

* cited by examiner

*Primary Examiner* — Niketa Patel
*Assistant Examiner* — Joseph Stoklosa
(74) *Attorney, Agent, or Firm* — Theresa A. Takeuchi; Steven M. Mitchell (57) ABSTRACT

Multifocal PVCs are detected and prevented. If the PVCs being detected have variable coupling intervals and significantly different morphologies, they are deemed multifocal and a prevention therapy is activated for a short period of time. In another embodiment, multifocality and the need for prevention therapy are determined based on morphology alone. Feedback mechanisms are used to adjust thresholds for coupling interval and morphology if the PVCs are considered not multifocal, but ventricular arrhythmia still occurs. In an embodiment, only morphologies are compared.

27 Claims, 7 Drawing Sheets

MULTIFOCAL PVC DETECTION FOR PREVENTION OF ARRHYTHMIAS

BACKGROUND OF THE INVENTION

1. Field of the Invention

The present invention is related to an implantable device for detecting premature ventricular contractions ("PVCs") and performing prevention therapy based thereon.

2. Background Art

PVCs are a fairly common type of irregular heart rhythm. They occur when the ventricles of the heart beat before receiving the correct electrical signal from the atria. Following this extra beat, a brief pause may occur as the conduction system of the heart resets itself. Two PVCs in a row are classified as a couplet.

PVCs are generally harmless. However, in patients with underlying heart disease, frequent PVCs may signify an increased risk of ventricular tachycardia, a potentially fatal arrhythmia. In some cases, the cause of PVCs is unknown. In other cases, they may be due to known causes such as anxiety, stress, fatigue, cardiac ischemia, past damage to the heart, or congenital heart disease, among other problems.

Individuals with PVCs may notice palpitations—a feeling that their heart is galloping, pounding, or skipping beats. These palpitations may indicate more serious heart problems.

A cardiac device and method are needed to detect PVCs and perform preventative therapy on the heart so that further arrhythmias may be avoided.

SUMMARY OF THE INVENTION

Multifocal PVCs may signify an increased risk of heart disease. The present invention is an algorithm and device for detecting multifocal PVCs.

In a first embodiment, when a first PVC is detected, its morphology and coupling interval are stored. After a second PVC is detected, the morphology and coupling interval of the second PVC are also stored. The coupling intervals of the two PVCs are compared. If the difference between the two coupling intervals is greater than a predetermined coupling interval threshold, the morphologies of the two PVCs are compared. If the difference between the two morphologies is greater than a predetermined morphology threshold, a preventative therapy is activated.

If the difference between the two coupling intervals is not greater than the predetermined coupling interval threshold, the PVC is deemed to be unifocal, not multifocal, and no preventative therapy is applied. However, if a ventricular arrhythmia ("VA") is detected after the PVC has been classified as unifocal, the predetermined coupling interval threshold is decreased.

Similarly, if the difference between the two morphologies is not greater than the predetermined morphology threshold, the PVC is deemed to be unifocal and no preventative therapy is applied. However, if a VA is detected after the PVC has been classified as unifocal, the predetermined morphology threshold is decreased.

In a second embodiment, only the morphologies of the PVCs are stored and compared.

These embodiments may be performed by an implantable device, such as an implantable cardioverter defibrillator ("ICD"), a pacemaker, or any other such device known to one of skill in the art. The invention may also be included in a non-implantable device such as, for example, a cardiac monitoring device of the type used in a clinical setting.

Further embodiments, features, and advantages of the present inventions, as well as the structure and operation of the various embodiments of the present invention, are described in detail below with reference to the accompanying drawings.

BRIEF DESCRIPTION OF THE DRAWINGS/FIGURES

The accompanying drawings, which are incorporated herein and form a part of the specification, illustrate the present invention, and, together with the description, further serve to explain the principles of the invention and to enable a person skilled in the pertinent art to make and use the invention.

The present invention will now be described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE INVENTION

The present invention is described in the environments of implantable stimulation devices such as an implantable cardioverter defibrillator ("ICD") and a dual-chamber pacemaker. These environments are described below. With this description of the invention, a person skilled in the art will recognize other applications for the invention including both implantable devices and non-implantable devices.

Figure 1:
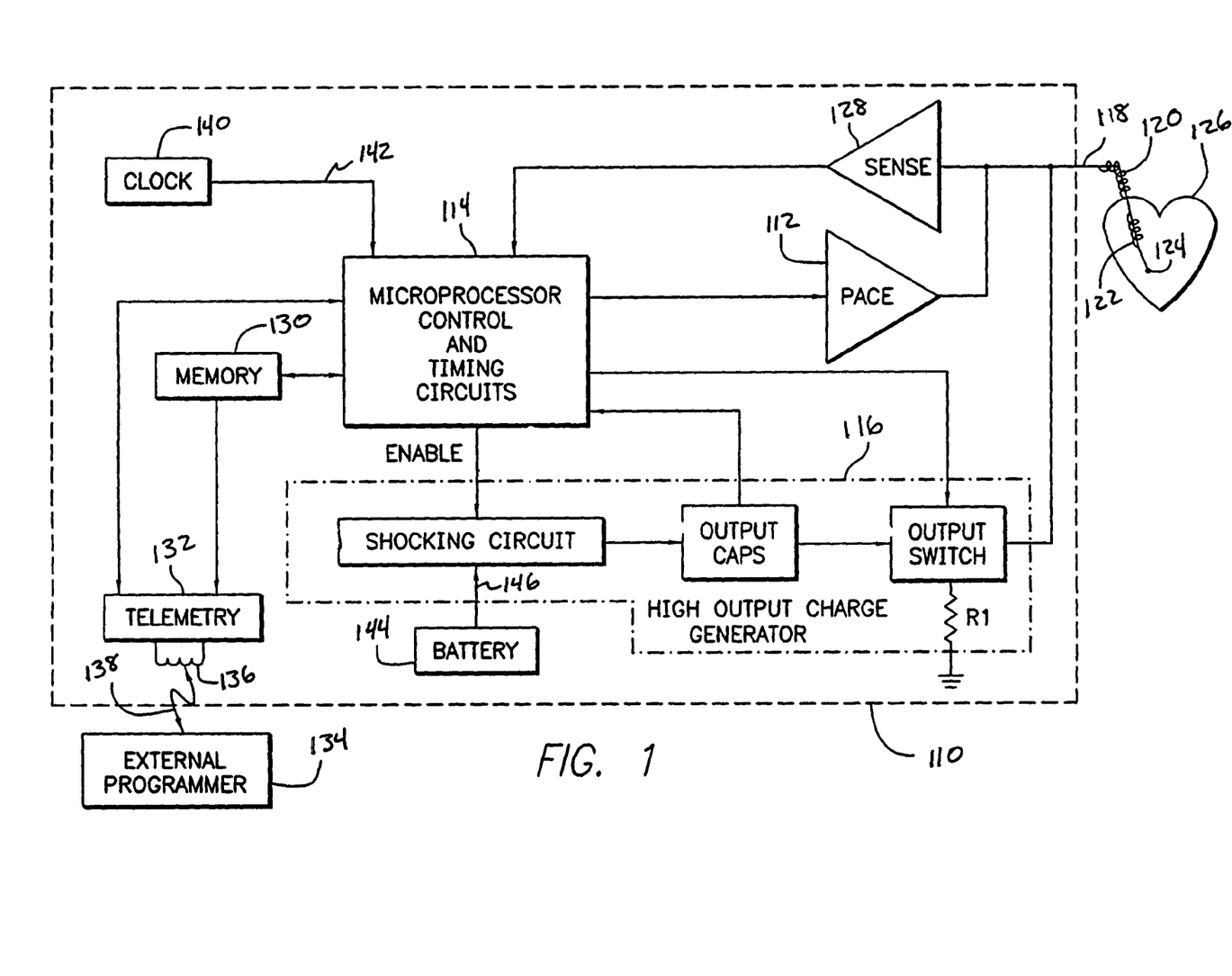
FIG. 1 is a simplified functional block diagram of a combined ICD and pacemaker, which represents one type of implantable stimulation device with which the present invention may be used.
Figure 2:
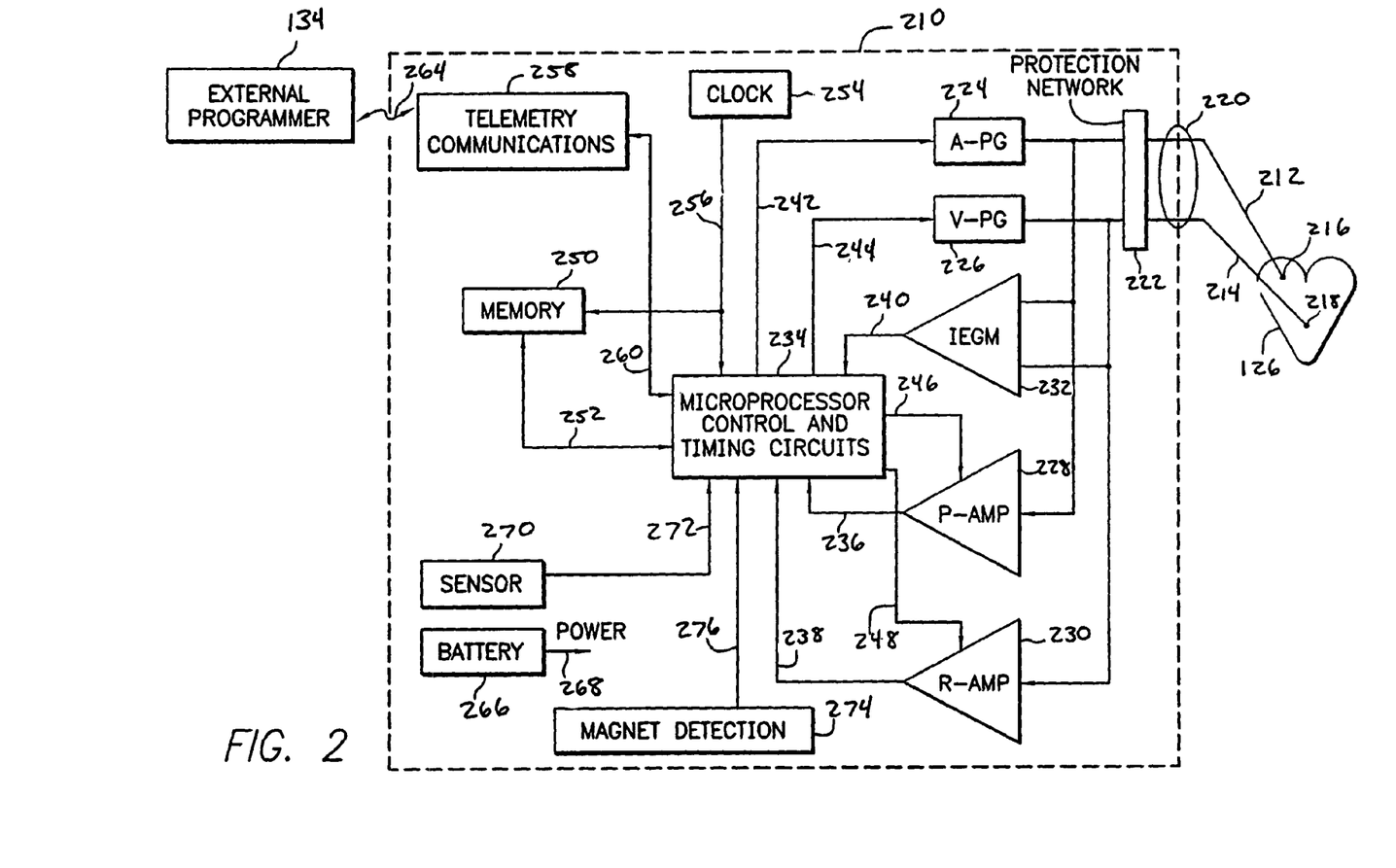
FIG. 2 is a functional block diagram of an implantable dual-chamber pacemaker, which represents another type of implantable medical device with which the present invention may be used.

In FIG. 1, there is shown a simplified functional block diagram of an ICD device 110, and in FIG. 2, there is shown a simplified functional block diagram of a dual-chamber pacemaker 210. It should be noted that the ICD 110 includes a pacing circuit 112 to combine the functionality of an ICD and a pacemaker within the same stimulation device.

It is the primary function of an ICD device to sense the occurrence of an arrhythmia, and to automatically apply an appropriate electrical shock therapy to the heart aimed at terminating the arrhythmia. To this end, the ICD device 110, as shown in the functional block diagram of FIG. 1, includes a control and timing circuit 114, such as a microprocessor, state-machine or other such control circuitry, that controls the ICD and pacemaker functions of the device 110.

With respect to the ICD function, a high output charge generator 116 is controlled by the circuit 114. The high output charge generator 116 generates electrical stimulation pulses of moderate or high energy (corresponding to the cardioversion or defibrillation pulses, respectively), e.g., electrical pulses having energies of about from 1 to 10 joules (moderate) or about 11 to 40 joules (high), as controlled by the control/timing circuit 114.

Such moderate or high energy pulses are applied to the patient's heart through at least one lead 118 and between at least two defibrillation electrodes, such as coil electrodes 120 and 122 or between one electrode, such as electrode 120, and the device enclosure or case 110. The lead 118 preferably also includes at least one electrode for pacing and sensing functions, such as electrode 124. Typically, the lead 118 is transvenously inserted into the heart so as to place the coil electrodes 120 and 122 in the apex of the heart and in the superior vena cava, respectively. While only one lead is shown in FIG. 1, it is to be understood that additional leads and electrodes may be used as desired or needed in order to efficiently and effectively apply to the patient's heart 126 the electrical therapy generated by the high voltage generator 116.

The ICD 110 also includes a sense amplifier 128. It is the function of the sense amplifier 128 (also referred to as a "sampler" or "sensing circuit") to sense (or sample) the electrical activity of the heart 126 to determine an electrogram signal. The electrogram signal includes, as is known in the art, R waves which occur upon the depolarization, and hence contraction, of ventricular tissue; and P waves which occur upon the depolarization, and hence contraction, of atrial tissue. Thus, by sensing R waves and/or P waves from the electrogram signal determined by the sense amplifier 128, the control/timing circuit 114 is able to make a determination as to the rate and regularity of the patient's heart beat and whether a pacing stimulation pulse should be delivered to the heart. Such information, in turn, also allows the control/timing circuit 114 to determine whether the heart 126 of a patient is experiencing a tachyarrhythmia, and to apply appropriate anti-tachyarrhythmia stimulation therapy. Further, as will be seen hereinafter, the electrogram signal is further utilized by the control/timing circuit 114 to extract a morphology template and coupling interval measurement. A morphology template shows the form and structure of an electrogram signal. A coupling interval measurement is the length of time between a normal sinus beat and an ensuing premature beat. Both morphology and coupling interval are utilized in embodiments of the present invention.

The control/timing circuit 114 further has a memory circuit 130 coupled thereto. The operating parameters and instructions used by the control/timing circuit 114 are stored in the memory circuit 130. Such operating parameters define, for example, the amplitude of each shock energy pulse to be delivered to the patient's heart 126 within each tier of therapy, as well as the duration of these shock pulses. The operating instructions define the method steps performed by circuit 114 to implement the ICD and pacemaker functions. The memory 130 may take many forms, and may be subdivided into as many different memory blocks or sections (addresses) as needed to store desired data and control information. Such data may include the morphology template and the coupling interval measurement.

Advantageously, the operating parameters of the implantable device 110 may be non-invasively programmed into the memory 130 through a telemetry circuit 132, in telecommunicative contact with an external programmer 134 by way of a suitable coupling coil 136. These operating parameters may include, for example, signal configuration, filtering pass band, and sampling rate. The coupling coil 136 may serve as an antenna for establishing a radio frequency (RF) communication link 138 with the external programmer 134; or the coil 136 may serve as a means for inductively coupling data to and from the telemetry circuit 132 from and to the external programmer 134, as is known in the art. See, e.g., U.S. Pat. Nos. 4,809,697 (Causey, III et al.) and 4,944,299 (Silvian), incorporated herein by reference. Further, a circuit such as telemetry circuit 132 advantageously allows status information relating to the operation of the ICD 110, as contained in the control/timing circuit 114 or memory 130, and the morphology templates and coupling interval measurements to be sent to the external programmer 134 through the established link 138.

The control/timing circuit 114 includes appropriate processing and logic circuits for analyzing the electrogram output of the sense amplifier 128 and determining if such signals indicate the presence of an arrhythmia. Typically, the control/timing circuit 114 is based on a microprocessor, or similar processing circuit, which includes the ability to process or monitor input signals (data) in a prescribed manner, e.g., as controlled by program code stored in a designated area or block of the memory 130. The details of the design and operation of the control/timing circuit 114 are not critical to the present invention. Rather, any suitable control/timing circuit 114 may be used that carries out the functions described herein. The use, design, and operation of microprocessor-based control circuits to perform timing and data analysis functions is known in the art.

The pacing pulse generator 112 may be of the type as described subsequently with respect to FIG. 2. It may provide for the delivery of pacing stimulation pulses to both the atria and ventricles. The control circuit 114, in analyzing the activity sensed by sensing circuit 128, provides for demand pacing. With "demand" pacing, pacing pulses are delivered only when there is an absence of natural R wave or P wave within an escape interval.

A clock circuit 140 directs an appropriate clock signal(s) to the control circuit 114, as well as to any other circuits throughout the ICD device 110 that require a clock signal (e.g., to the memory 130) by way of clock bus 142.

The ICD device 110 additionally includes a battery 144. The battery 144 provides operating power to all of the circuits of the ICD device 110 via a power line 146.

In FIG. 2, a simplified block diagram of the circuitry needed for a dual-chamber pacemaker 210 is illustrated. The pacemaker 210 is coupled to a heart 126 by way of leads 212 and 214, the lead 212 having an electrode 216 that is in contact with one of the atria of the heart, and the lead 214 having an electrode 218 that is in contact with one of the ventricles of the heart. The leads 212 and 214 are electrically and physically connected to the pacemaker 210 through a connector 220 that forms an integral part of the housing wherein the circuits of the pacemaker are housed.

The connector 220 is electrically connected to a protection network 222, which network 222 electrically protects the circuits within the pace-maker 210 from excessive shocks or voltages that could appear on the electrodes 216 and/or 218 in the event such electrodes were to come in contact with a high voltage signal, e.g., from a defibrillation shock.

The leads 212 and 214 carry stimulating pulses to the electrodes 216 and 218 from an atrial pulse generator (A-PG) 224 and a ventricular pulse generator (V-PG) 226, respectively. Further, electrical signals from the atria are carried from the electrode 216, through the lead 212, to the input terminal of an atrial channel sense amplifier (P-AMP) 228; and electrical signals from the ventricles are carried from the electrode 218, through the lead 214, to the input terminal of a ventricular channel sense amplifier (R-AMP) 230. Hence, the amplifiers 228 and 230 each determines an electrogram signal. The electrogram signal of amplifier 228 contains mainly atrial activity of the heart, and the electrogram signal of amplifier 230 contains mainly ventricular activity of the heart. Either one or both electrograms may be utilized for practicing the present invention.

Similarly, electrical signals from both the atria and ventricles are applied to the inputs of an IEGM (intracardiac electrogram) amplifier 232. The amplifier 232 is typically configured to detect an evoked response from the heart 126 in response to an applied stimulus, thereby aiding in the detection of "capture." Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue.

The dual-chamber pacemaker 210 is controlled by a control/timing circuit 234 that typically includes a microprocessor programmed to carry out control and timing functions and morphology characteristic extraction and quantifying in accordance with the present invention. The control/timing circuit 234 receives the electrogram signal from the atrial (P-AMP) amplifier 228 over signal line 236. Similarly, control/timing circuit 234 receives the electrogram signal from the ventricular (R-AMP) amplifier 230 over signal line 238, and the output signals from the IEGM amplifier 232 over signal line 240. These electrograms permit detection signals to be generated each time that a P wave or an R wave or an evoked response occurs within the heart 126. Control/timing circuit 234 also generates trigger signals that are sent to the atrial pulse generator (A-PG) 224 and the ventricular pulse generator (V-PG) 226 over signal lines 242 and 244, respectively. These trigger signals are generated each time that a stimulation pulse is to be generated by the respective pulse generator 224 or 226. The atrial trigger signal is referred to simply as the "A-trigger," and the ventricular trigger signal is referred to as the "V-trigger."

During the time that either an A-pulse or V-pulse is being delivered to the heart, the corresponding amplifier, P-AMP 228 and/or R-AMP 230, is typically disabled by way of a blanking signal presented to these amplifiers from control/timing circuit 234 over signal lines 246 and 248, respectively. This blanking action prevents the amplifiers 228 and 230 from becoming saturated from the relatively large stimulation pulses that are present at their input terminals during this time. This blanking action also helps prevent residual electrical signals present in the muscle tissue as a result of the pacemaker stimulation from being interpreted as P waves or R waves.

As shown in FIG. 2, the pacemaker 210 further includes a memory circuit 250 that is coupled to control/timing circuit 234 over a suitable data/address bus 252. This memory circuit 250 allows certain control parameters, used by the control/timing circuit 234 in controlling the operation of the pacemaker, to be programmably stored and modified, as required, in order to customize the pacemaker's operation to suit the needs of a particular patient. Further, data, such as the morphology templates or coupling interval measurements, determined or sampled during the operation of the pacemaker may be stored in the memory 250 for later retrieval and analysis.

As with the memory 130 of the ICD device 110 shown in FIG. 1, the memory 250 of the pacemaker 210 (FIG. 2) may take many forms. It may be subdivided into as many different memory blocks or sections (addresses) as needed in order to allow desired data and control information to be stored.

A clock circuit 254 directs an appropriate clock signal(s) to the control/timing circuit 234, as well as to any other needed circuits throughout the pacemaker 210 (e.g., to the memory 250) by way of clock bus 256.

A telemetry/communications circuit 258 is further included in the pacemaker 210. This telemetry circuit 258 is connected to the control/timing circuit 234 by way of a suitable command/data bus 260. In turn, the telemetry circuit 258, which is included within the implantable pacemaker 210, may be selectively coupled to an external programming device 134 by means of an appropriate communication link 264, which communication link 264 may be any suitable electromagnetic link, such as an RF (radio frequency) channel, a magnetic link, an inductive link, an optical link, and the like. Advantageously, through the external programmer 134 and the communication link 264, desired commands may be sent to the control/timing circuit 234. Similarly, through this communication link 264 with the programmer 134, data commands (either held within the control/timing circuit 234, as in a data latch, or stored within the memory 250) may be remotely received from the programmer 134. Similarly, data initially sampled through the leads 212 or 214, and processed by the microprocessor control/timing circuit 234, or other data, such as the morphology templates and coupling interval measurements, measured within or by the pacemaker 210, may be stored and uploaded to the programmer 134 for display. In this manner, non-invasive communications can be established with the implanted pacemaker 210 from a remote, non-implanted location.

The pacemaker 210 additionally includes a battery 266. The battery 266 provides operating power to all of the circuits of the pacemaker 210 via a POWER signal line 268.

It is noted that the pacemaker 210 in FIG. 2 is referred to as a dual-chamber pacemaker because it interfaces with both the atria and the ventricles of the heart. Those portions of the pacemaker 210 that interface with the atria, e.g., the lead 212, the P wave sense amplifier 228, the A-pulse generator 224, and corresponding portions of the control/timing circuit 234, are commonly referred to as the "atrial channel." Similarly, those portions of the pacemaker 210 that interface with the ventricles, e.g., the lead 214, the R wave sense amplifier 230, the V-pulse generator 226, and corresponding portions of the control/timing circuit 234, are commonly referred to as the "ventricular channel."

The pacemaker 210 further includes an activity sensor 270 that is connected to the control/timing circuit 234 of the pacemaker 210 over a suitable connection line 272. The sensor 270 may be of the type well known in the art.

The pacemaker 210 further includes magnet detection circuitry 274, coupled to the control/timing circuit 234 over signal line 276. It is the purpose of the magnet detection circuitry 274 to detect when a magnet is placed over the pacemaker, which magnet may be used by a physician or other medical personnel to perform various reset functions of the pacemaker 210, and/or to signal the control/timing circuit 234 that an external programmer 134 is in place to receive data from, or send data to, the pacemaker memory 250 or control/timing circuit 234 through the telemetry communications circuits 258.

As with the ICD device 110 of FIG. 1, the telemetry or communications circuit 258 may be of conventional design, such as is described in U.S. Pat. No. 4,944,299, or as is otherwise known in the art. Similarly, the external programmer 134 may be of any suitable design known in the art, such as is described in U.S. Pat. No. 4,809,697. Likewise, the memory circuit 250, and the circuits utilized in the atrial and ventricular channels may all be of common design as is known in the pacing art. The present invention is not concerned with the details of the circuitry utilized for each of these pacing elements. Rather, it is concerned with the manner in which all of these pacing elements cooperate with each other in order to provide a particular pacing mode of operation. Such cooperation is controlled by the control/timing circuit 234.

The control/timing circuit 234 may be realized using a variety of different techniques and/or circuits. The preferred type of control/timing circuit 234 is a microprocessor-based control/timing circuit. It is noted, however, that the control/timing circuit 234 could also be realized using a state machine. Indeed, any type of control circuit or system could be employed for the control/timing circuit 234. The present invention is likewise not concerned with the details of the control/timing circuits 114 and 234. Rather, it is concerned with the end result achieved by the control/timing circuit. That is, so long as the control/timing circuit 234 controls the operation of the pacemaker (or other medical device) so that the desired functions are achieved as set forth herein, e.g., by following the steps described below in the flow charts of FIGS. 5 and 6, it matters little what type of control/timing circuit is used. Those of skill in the implantable medical device art, given the teachings presented herein, should thus be able to fashion numerous different types of control/timing circuits or circuits that achieve the desired device control.

Representative of the types of control/timing circuits that may be used with the invention is the microprocessor-based control/timing circuit described in U.S. Pat. No. 4,940,052, entitled "Microprocessor Controlled Rate-Responsive Pacemaker Having Automatic Rate Response Threshold Adjustment." Reference is also made to U.S. Pat. Nos. 4,712,555 and 4,944,298, wherein a state-machine type of operation for a pacemaker is described; and U.S. Pat. No. 4,788,980, wherein the various timing intervals used within the pacemaker and their inter-relationship are more thoroughly described. The '052, '555, '298 and '980 patents are incorporated herein by reference.

Figure 3:
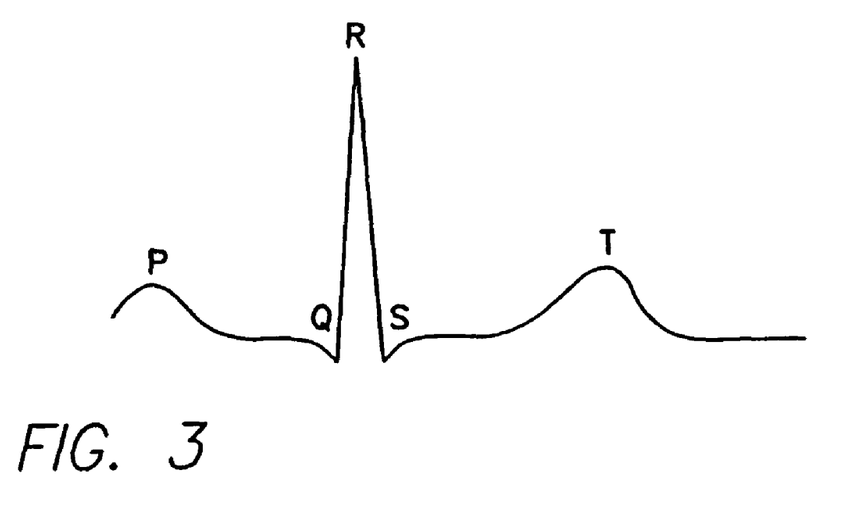
FIG. 3 is an electrogram illustrating a single cardiac cycle of a healthy heart.

FIG. 3 is a typical or normal electrogram (EGM) illustrating the conventional nomenclature for a cardiac cycle of the heart. The beginning of the cardiac cycle is initiated by a P wave which is normally a small positive wave. It is the activation of the atria, forcing them to contract. Following the P wave there is an EGM portion which is substantially constant in amplitude. This substantially constant portion will have a time duration on the order of, for example, 120 milliseconds.

The QRS complex of the EGM then normally occurs after the substantially constant portion with a Q wave which is normally a small negative deflection which is immediately succeeded by the R wave which is a rapid positive deflection. The R wave, which generally has an amplitude greater than any other waves of the EGM signal and will have a spiked shape of relatively short duration with a sharp rise and a sharp decline, represents contraction or depolarization of the ventricles. The R wave may have a duration on the order of about 40 milliseconds.

Following the R wave, the QRS complex is completed with an S wave. The S wave may be generally characterized by a small positive inflection in the EGM signal.

Following the S wave is the T wave. The T wave is relatively long in duration, for example, on the order of about 150 milliseconds. Following the T wave is a substantially constant amplitude until the next P wave occurs to begin the next cardiac cycle.

Figure 4A:
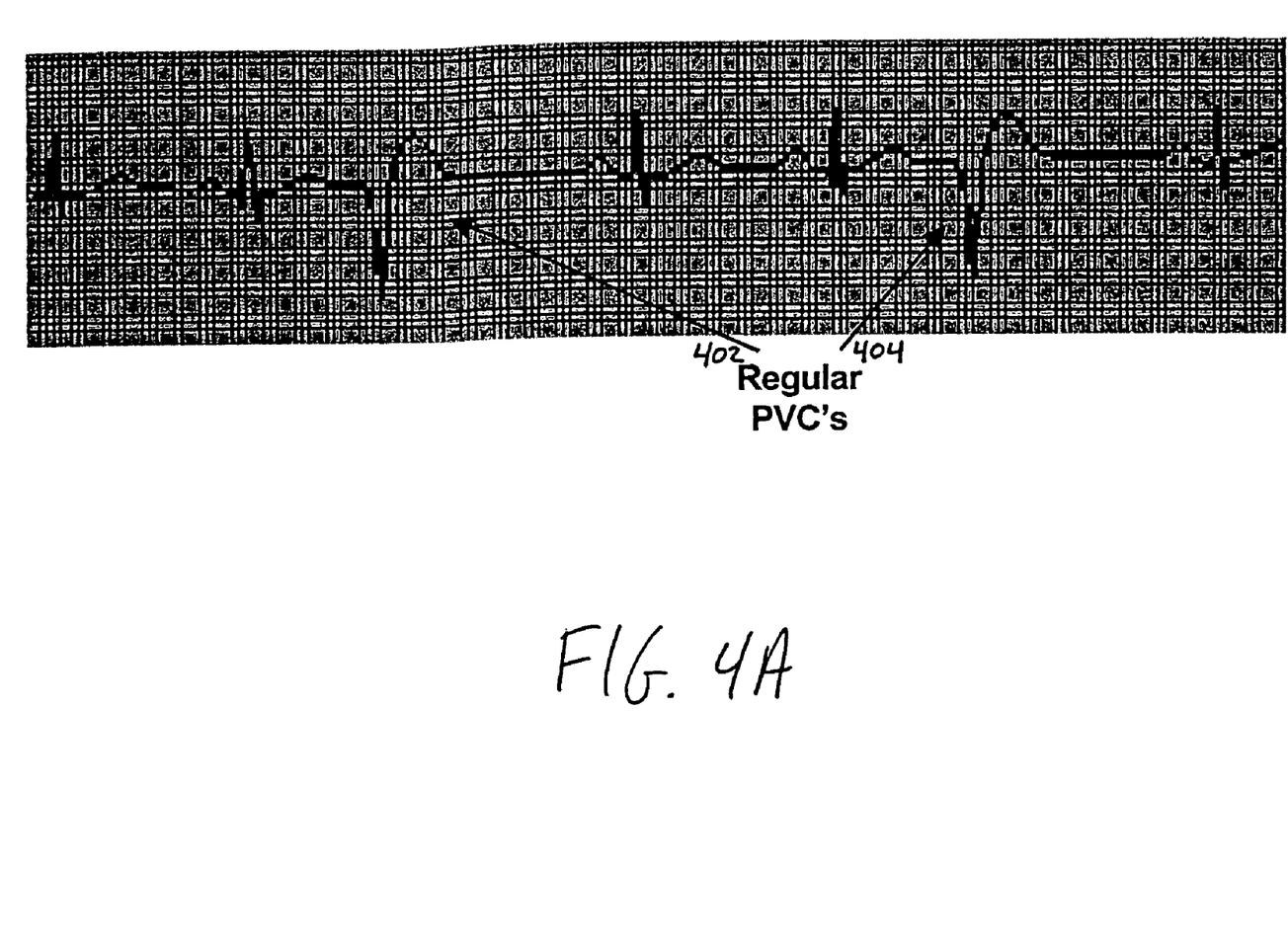
FIG. 4A is an illustration of a unifocal PVC in an electrocardiogram ("EKG") signal.

FIG. 4A is an illustration of a unifocal PVC in an electrocardiogram (EKG) signal. PVCs can be classified according to where they arise within the heart. Unifocal PVCs 402 and 404 arise from the same source with respect to one another, so they look the same on an EKG.

Figure 4B:
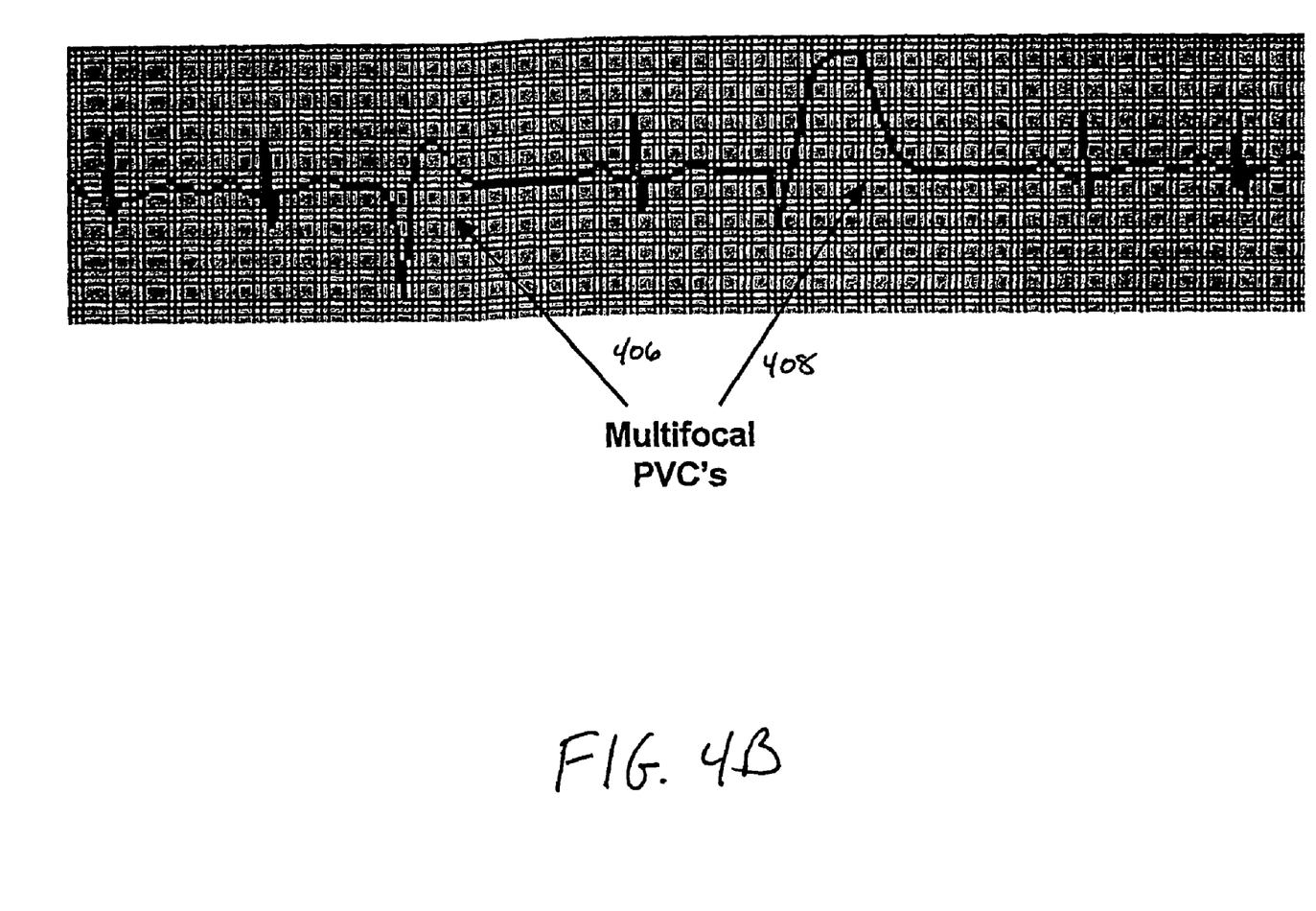
FIG. 4B is an illustration of a multifocal PVC in an EKG signal.

FIG. 4B is an illustration of a multifocal PVC in an EKG signal. Multifocal PVCs 406 and 408 arise from different sources. This makes them look different from each other on an EKG.

It has been shown that multifocal PVCs with different QRS morphologies carry more prognostic value than unifocal PVCs with a single morphology. (See, A. Katz, Arrhythmias: Clinical Manifestations, in *Physiology of the Heart*, at 581-629 (Lippincott Williams & Williams, $3^{rd}$ ed. 2001), incorporated herein by reference in its entirety.) Moreover, multifocal PVCs have been called transitional arrhythmias. (See, K. Kessler et al., *Multiform Ventricular Complexes: A Transitional Arrhythmia Form?*, Am Heart. J. 118:441-444 (1989), incorporated herein by reference in its entirety.) Therefore, a preventative pacing algorithm which attempts to minimize PVCs, or which is otherwise triggered by a high PVC count, should be particularly sensitive to multifocal PVCs. Measuring unifocal PVCs does not give sufficient information to correctly determine whether preventative pacing is needed. Performing preventative pacing or other type of prevention therapy only after determining that the PVCs are multifocal ensures that the preventative therapy is not performed unnecessarily. Multifocal PVCs can be detected by using a morphology algorithm, by measuring coupling interval variability, or by using both for greater specificity.

Figure 5:
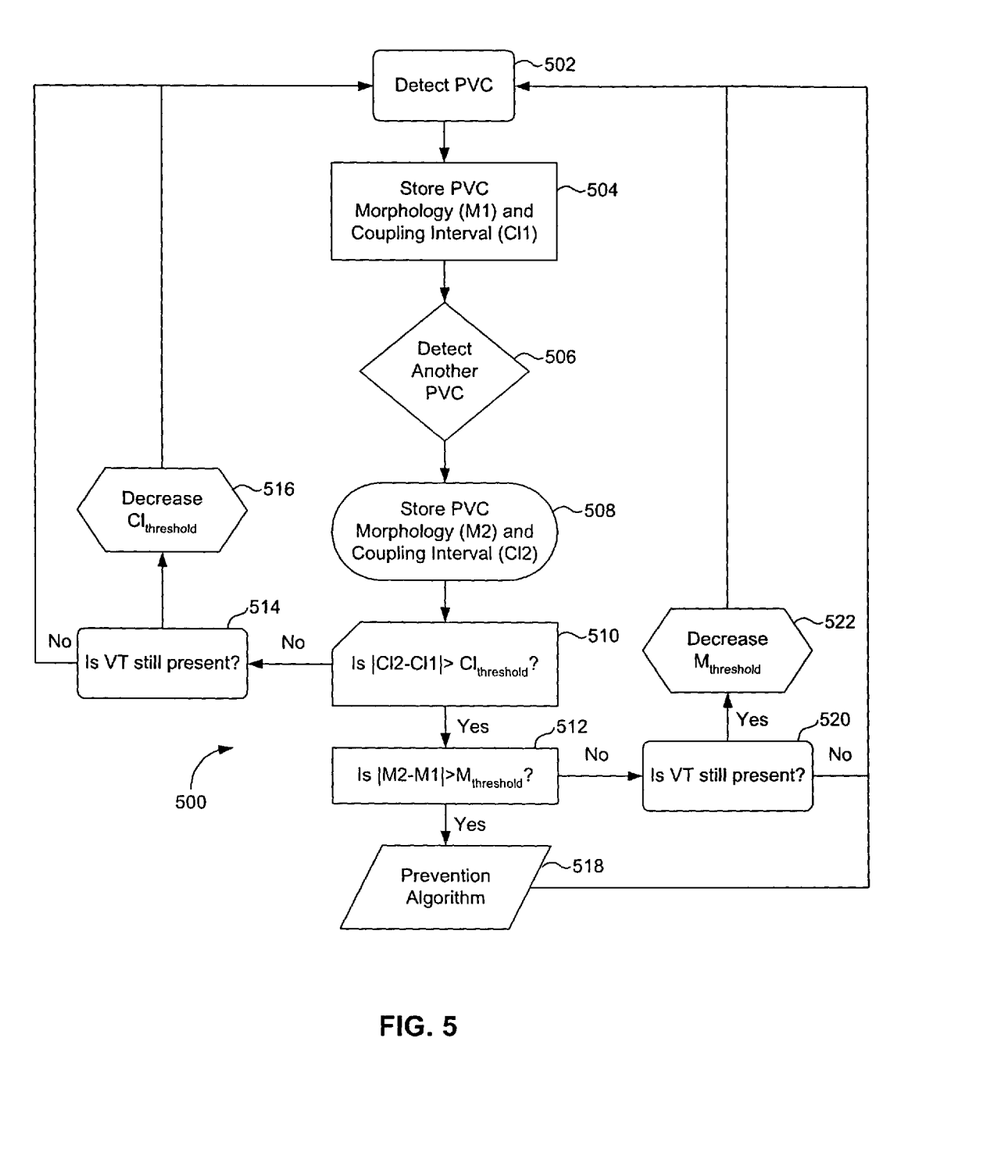
FIG. 5 is a flowchart representing one embodiment of the present invention.

FIG. 5 is a flowchart representing a method 500 by which multifocal PVCs can be detected and prevented. For ease of explanation, reference will be made to the device of FIG. 1. However, one of skill in the art will recognize that these steps may be implemented on any similar type of device (including, for example, the device of FIG. 2). In step 502, a PVC is detected. In one embodiment, a PVC is determined to have occurred when the R-R interval between two consecutive beats is shorter than an average R-R interval. For example, a current R-R interval may be compared to an average of, for example, the ten previous R-R intervals. This determination may be made by, for example, control/timing circuit 114, after it receives an electrogram signal from sensing circuit 128. One of skill in the art will recognize that other methods of PVC detection may be used. Once the first PVC is detected, method 500 advances to step 504.

Coupling interval alone does not relay sufficient information concerning the origin of a PVC. Therefore, in step 504, both a morphology of the first PVC and a coupling interval of the first PVC are stored in memory 130. The morphology and coupling interval information is typically measured when an electrogram signal is produced by sensing circuit 128. Any type of morphology algorithm could be used for the morphology measurement, as will be evident to one skilled in the art. For instance, in one embodiment, control/timing circuit 114 may quantify and save specific characteristics of the morphology. In another embodiment, the entire morphology waveform is stored.

Since the coupling interval is the length of time between a normal sinus beat and an ensuing beat, this interval can also be measured by control/timing circuit 114 from the electrogram signal produced by sensing circuit 128. In one embodiment, the coupling interval may be the length of time between consecutive R waves. This measurement is also referred to as the R-R coupling interval. In another embodiment, the coupling interval may be the length of time between a P wave and the following R wave. This measurement is also referred to as a P-R coupling interval.

Instructions for the control/timing circuit to take the morphology and coupling interval measurements may be automatically programmed into the implantable device, or they may be requested by external programmer 134. For purposes of explanation, the morphology of the first PVC stored will be referred to as M1. Likewise, the coupling interval of the first PVC will be referred to as CI1.

In step 506, a second PVC is detected by sensing circuit 128. Once the second PVC is detected, method 500 proceeds to step 508.

In step 508, a morphology of the second PVC and a coupling interval of the second PVC are stored in memory 130. In the same manner as above, the morphology of the second PVC will be referred to as M2, and the coupling interval of the second PVC will be referred to as CI2.

Method 500 then advances to step 510. In step 510, the difference in the coupling intervals of the first and second PVCs (|CI2−CI1|) is determined and then compared to a predetermined coupling interval threshold $CI_{threshold}$. This predetermined threshold $CI_{threshold}$ may be stored in memory 130. The comparison between the difference and the threshold may be made by several devices. In one embodiment, the comparison is made by a comparing circuit within control circuitry of the ICD, for example, control circuit 114. In another embodiment, the comparison may be made by external programmer 134. If the coupling interval difference is greater than the coupling interval threshold (|CI2−CI1|>$CI_{threshold}$), method 500 advances to step 512.

If the coupling interval difference is less than the coupling interval threshold (|CI2−CI1|<$CI_{threshold}$), prevention therapy is not needed, and method 500 advances to step 514.

While the terms "greater than" and "less than" are used herein in connection with comparisons to thresholds, a person skilled in the art will recognize that "greater than" could be replaced with "greater than or equal to" and/or that "less than" could be replaced with "less than or equal to" depending on the choice of the threshold value. Which operator to actually use is a design choice. Thus, as used herein, the term "greater than" may also include "greater than or equal to" and the term "less than" may also include "less than or equal to."

In step 514, the presence of a ventricular arrhythmia ("VA") is determined by, for example, control/timing circuit 114. In one embodiment, control/timing circuit 114 tests for the presence of a VA by measuring the interval between consecutive R waves. If the R-R interval being tested is shorter than an average of, for example, the previous 10 R-R intervals, control/timing circuit 114 will identify the event as an arrhythmia. If the R-R interval being tested is not shorter than the average, no arrhythmia is deemed to have occurred, and method 500 returns to step 502. One of skill in the art will recognize that other methods of detecting VAs may be used.

If VAs are still present, method 500 advances to step 516. In step 516, the coupling interval threshold $CI_{threshold}$ is decreased. Method 500 then returns to step 502.

In step 510, if the difference between C1 and C2 is greater than coupling interval threshold $CI_{threshold}$, the method advances to step 512. In step 512, morphologies M1 and M2 are compared. Several methods may be used for this comparison. For example, in one embodiment, the QRS complex from M1 is aligned with the QRS complex from M2. The difference in the areas under the QRS waveforms is calculated, and a match score is assigned. The match score is proportional to the difference in areas under the QRS waveforms. The match score may be, for example, a percentage.

If the difference between M1 and M2 is greater than a predetermined morphology threshold $M_{threshold}$ (|M2−M1|>$M_{threshold}$), the PVCs are considered multifocal, meaning that their origins differ. $M_{threshold}$ may be determined on a case-by-case basis. In one embodiment, $M_{threshold}$ is an average match score of a patient's morphologies from several beats where no PVCs are present. If the PVCs are considered multifocal, method 500 advances to step 518.

In step 518, a prevention therapy is performed to diminish or eliminate the occurrence of multifocal PVCs. For example, pacing circuit 112 may activate a period of overdrive pacing for a period of time. It will be apparent to one having skill in the art that other prevention therapies may be used.

After the completion of step 518, method 500 returns to step 502.

If, in step 512, the difference between M1 and M2 is less than $M_{threshold}$, method 500 advances to step 520. In step 520, the presence of VAs is determined by control/timing circuit 114. The presence of the VA may be determined, for example, in the same manner as discussed above with respect to step 514. If no VAs are detected, method 500 returns to step 502. If a VA is detected, method 520 proceeds to step 522.

In step 522, morphology threshold $M_{threshold}$ is decreased. Method 500 then returns to step 502.

Figure 6:
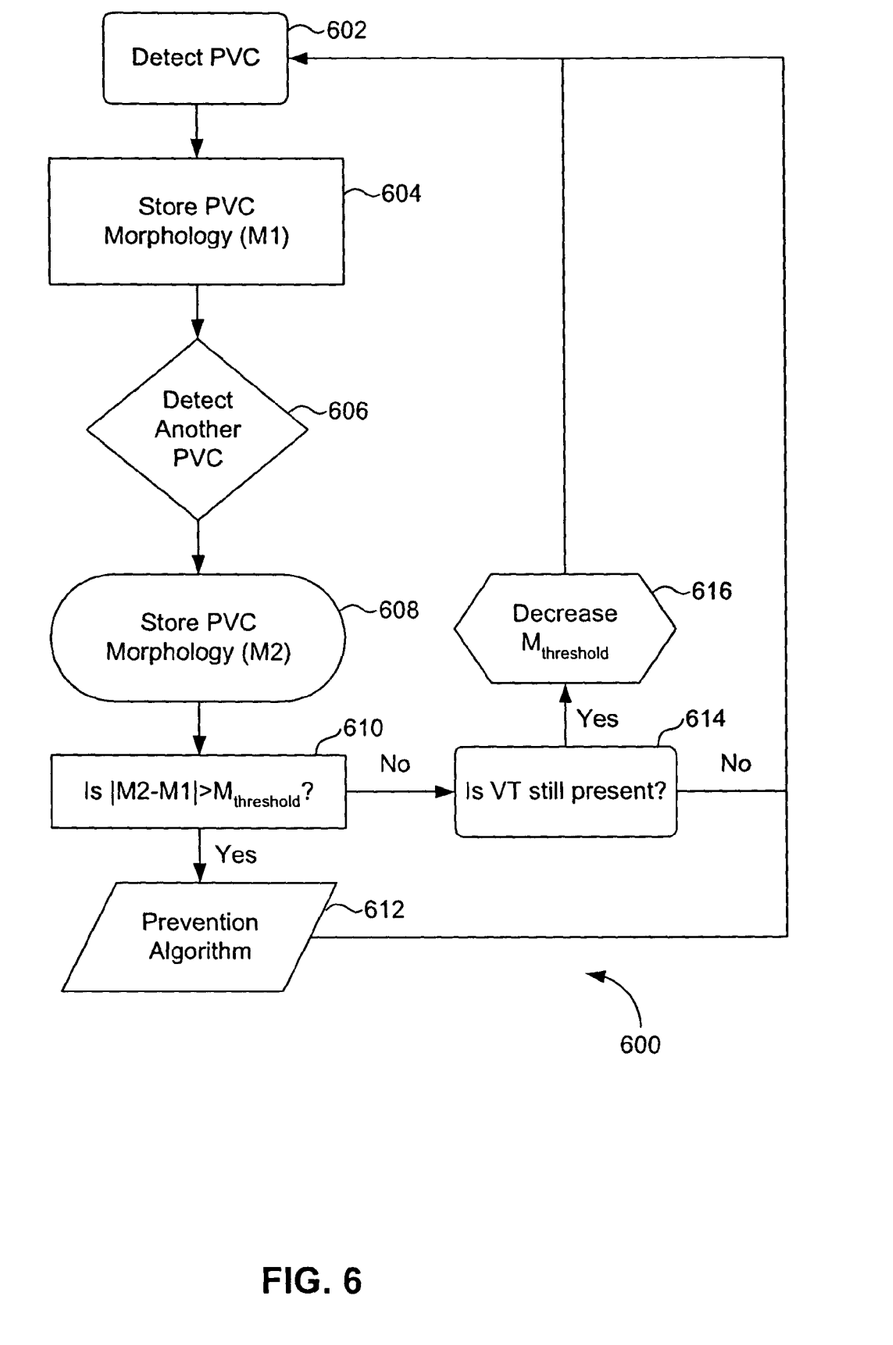
FIG. 6 is a flowchart representing another embodiment of the present invention.

FIG. 6 is a flowchart representing a method 600, which describes a second embodiment of the present invention. Instead of comparing morphologies and coupling intervals of two PVCs, method 600 compares morphologies without checking the coupling interval first. This embodiment decreases the specificity of the detection, because only one measurement is made for each PVC. However, sensitivity is increased because the morphologies for all PVCs are examined, not just those whose coupling intervals exceed $CI_{threshold}$. Also, less computing power and memory is required, since coupling intervals need not be analyzed or stored.

Method 600 begins with step 602. In step 602, a first PVC is detected by sensing circuit 128. The methods of detection are the same as those discussed above with respect to step 502. Once a first PVC is detected, method 600 advances to step 604.

In step 604, the morphology of the first PVC (again referred to as M1) is stored in memory 130. Method 600 then proceeds to step 606.

In step 606, a second PVC is detected by sensing circuit 128, and method 600 proceeds to step 608.

In step 608, the morphology of the second PVC (M2) is stored in memory 130. Method 600 advances to step 610 after storage is complete.

When step 610 is reached, the difference between the morphologies of the first and second PVCs is determined (|M2−M1|). This difference is then compared to predetermined morphology threshold $M_{threshold}$. As with method 500, these calculations may be made by the implanted device or by an external programmer. If the difference between the morphologies is greater than the morphology threshold (|M2−M1|>$M_{threshold}$), method 600 advances to step 612.

In step 612, a prevention therapy is performed. This prevention therapy may be similar to that discussed above with respect to step 518. Upon completion of the prevention therapy, method 600 returns to step 602.

If the difference between the morphologies is not greater than the morphology threshold (|M2−M1| # $M_{threshold}$), method 600 proceeds to step 614.

Step 614 determines whether a VA is still detected by sensing circuit 128. If no VA is detected, method 600 returns to step 602. If a VA is still present, method 600 proceeds to step 616.

In step 616, the morphology threshold $M_{threshold}$ is decreased. Method 600 then returns to step 602.

CONCLUSION

Thus, an implantable cardiac device and method for detecting and preventing PVCs are provided. While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A method of detecting and preventing ventricular arrhythmias, comprising:
   a. determining an electrogram or electrocardiogram signal;
   b. detecting at least two premature ventricular contractions (PVCs);
   c. determining a difference between morphologies of the at least two PVCs;
   d. comparing said difference to a predetermined morphology threshold using a microprocessor; and
   e. delivering preventive therapy based on said comparing step.

2. The method of claim 1, wherein step (e) comprises determining whether to deliver preventative therapy based on step (d) and delivering therapy when it is determined that therapy should be delivered.

3. The method of claim 1, wherein step (e) comprises:
   delivering overdrive pacing.

4. The method of claim 1, wherein step (e) comprises:
   determining that preventive therapy should be delivered when the difference is greater than the morphology threshold; and
   determining that preventive therapy should not be delivered when the difference is less than the morphology threshold.

5. The method of claim 2, further comprising a step after step (e) of:
   narrowing said morphology threshold when a ventricular arrhythmia is detected after determining that preventative therapy should not be delivered.

6. The method of claim 1, further comprising before step (d):
   determining a difference between coupling intervals of the at least two PVCs; and
   comparing the difference between the coupling intervals to a predetermined coupling interval threshold.

7. The method of claim 6, wherein step e further comprises:
   determining that preventive therapy should not be delivered when the difference between the coupling intervals is less than the predetermined coupling interval threshold.

8. The method of claim 7, further comprising after step e:
   reducing said coupling interval threshold when a ventricular arrhythmia is detected after determining that preventative therapy should not be delivered.

9. The method of claim 8, wherein said coupling intervals are P-R coupling intervals.

10. The method of claim 8, wherein said coupling intervals are R-R coupling intervals.

11. The method of claim 1, wherein step (c) comprises
    i. aligning a QRS complex from each of the at least two PVCs;
    ii. measuring a difference in areas under QRS waveforms in the QRS complexes; and
    iii. assigning a match score that is proportional to the difference in step (ii).

12. The method of claim 11, wherein said predetermined morphology threshold is an average match score of at least two non-PVC beats.

13. An apparatus configured to detect and prevent ventricular arrhythmias, comprising:
    detecting means configured to detect at least two premature ventricular contractions (PVCs);
    processing means configured to determine a difference between morphologies of each of the at least two PVCs;
    comparing means configured to compare said difference to a predetermined morphology threshold; and
    delivering means configured to deliver preventative therapy based on said comparison.

14. The apparatus of claim 13, wherein said delivering means is configured to deliver preventative therapy if the difference between the morphologies is greater than the predetermined morphology threshold.

15. The apparatus of claim 13, wherein said processor means is further configured to narrow the predetermined morphology threshold when a ventricular arrhythmia is detected after the difference between the morphologies is determined to be less than the predetermined morphology threshold.

16. The apparatus of claim 13, wherein:
    said processing means is further configured to determine a difference between coupling intervals of each of the at least two PVCs; and
    said comparing means is further configured to compare said difference between the coupling intervals to a predetermined coupling interval threshold.

17. An implantable cardiac device, comprising:
    a sensing circuit configured to sense at least two premature ventricular contractions (PVCs);
    a comparing circuit configured to compare a difference between morphologies of each of the at least two PVCs to a predetermined morphology threshold; and
    a pacing circuit configured to deliver preventative therapy based on said comparison.

18. The device of claim 17, wherein said pacing circuit is configured to deliver the preventative therapy when the difference between the morphologies is greater than the predetermined morphology threshold.

19. The device of claim 17, further comprising a control system configured to reduce the predetermined morphology threshold when a ventricular arrhythmia is detected after the difference between the morphologies is determined to be less than the predetermined morphology threshold.

20. The device of claim 17, wherein said comparing circuit is further configured to compare a difference between coupling intervals of each of the at least two PVCs to a predetermined coupling interval threshold.

21. The device of claim 20, wherein said pacing circuit is configured to deliver preventative therapy when the difference between the coupling intervals is greater than the predetermined coupling interval threshold.

22. The device of claim 20, further comprising a control system configured to reduce the predetermined coupling interval threshold when a ventricular arrhythmia is detected after the difference between the coupling intervals is determined to be less than the predetermined coupling interval threshold.

23. A method of detecting and preventing ventricular arrhythmias, comprising:
    a. determining an electrogram or electrocardiogram signal;
    b. detecting at least two premature ventricular contractions (PVCs);
    c. determining a difference between coupling intervals of the at least two PVCs;

d. comparing said difference between coupling intervals to a predetermined coupling interval threshold using a microprocessor;
e. determining a difference between morphologies of the at least two PVCs;
f. comparing said difference between morphologies to a predetermined morphology threshold using the microprocessor; and
g. delivering preventative therapy based on said comparing steps (d) and (f).

24. The method of claim 23, wherein step (g) comprises determining whether to deliver preventative therapy based on said comparing steps d and f and delivering therapy when it is determined that therapy should be delivered.

25. The method of claim 23, wherein step (g) comprises: delivering overdrive pacing.

26. The method of claim 23, wherein step g comprises:
determining that preventative therapy should be delivered when the difference between coupling intervals is greater than the coupling interval threshold and the difference between morphologies is greater than the morphology threshold; and
determining that preventative therapy should not be delivered when the difference between coupling intervals is less than the coupling interval threshold or the difference between morphologies is less than the morphology threshold.

27. A method of detecting and preventing ventricular arrhythmias, comprising:
a. determining an electrogram or electrocardiogram signal;
b. detecting at least two premature ventricular contractions (PVCs);
c. comparing said difference between coupling intervals of said at least two PVCs to a coupling interval threshold using a microprocessor;
d. repeating steps (a)-(c) when said difference between coupling intervals is less than the coupling interval threshold;
e. comparing a difference in morphologies of said at least two PVCs to a morphology threshold when said difference between coupling intervals is greater than the coupling interval threshold using the microprocessor; and
f. delivering therapy when said difference in morphologies is greater than the morphology threshold.

\* \* \* \* \*